US008154571B2

(12) United States Patent
Tobita et al.

(10) Patent No.: US 8,154,571 B2
(45) Date of Patent: Apr. 10, 2012

(54) THERMAL RECORDING MATERIAL CONTAINING TRIS(2- METHYL- 4-HYDROXY-5-T-BUTYL- PHENYL)BUTANE

(75) Inventors: Etsuo Tobita, Tokyo (JP); Koichi Shigeno, Tokyo (JP); Satoru Kanda, Tokyo (JP); Ryozo Arata, Tokyo (JP); Yamahiko Egami, Tokyo (JP)

(73) Assignee: Adeka Corporation, Tokyo (JP)

( * ) Notice: Subject to any disclaimer, the term of this patent is extended or adjusted under 35 U.S.C. 154(b) by 181 days.

(21) Appl. No.: 12/745,782

(22) PCT Filed: Dec. 25, 2008

(86) PCT No.: PCT/JP2008/073577

§ 371 (c)(1),
(2), (4) Date: Jun. 2, 2010

(87) PCT Pub. No.: WO2009/087909

PCT Pub. Date: Jul. 16, 2009

(65) Prior Publication Data

US 2010/0249466 A1 Sep. 30, 2010

(30) Foreign Application Priority Data

Jan. 10, 2008 (JP) ................................ 2008-003447

(51) Int. Cl.
*G01D 9/00* (2006.01)
*C07C 39/16* (2006.01)
*B41M 5/337* (2006.01)

(52) U.S. Cl. ...................................... 346/76.1; 568/720

(58) Field of Classification Search .................. 568/720
See application file for complete search history.

(56) References Cited

U.S. PATENT DOCUMENTS

| | | | |
|---|---|---|---|
| 4,319,051 | A | 3/1982 | Suenobu et al. |
| 4,467,119 | A | 8/1984 | Thomas |
| 4,473,831 | A | 9/1984 | Watanabe |
| 4,801,757 | A | 1/1989 | Smith |

FOREIGN PATENT DOCUMENTS

| | | |
|---|---|---|
| JP | 39-004469 | 4/1964 |
| JP | 56-040629 | 4/1981 |
| JP | 58-057990 | 4/1983 |
| JP | 58-087089 | 5/1983 |
| JP | 01-301634 | 12/1989 |
| JP | 9-058134 | 3/1997 |
| JP | 3816132 | 8/2006 |

OTHER PUBLICATIONS

International Search Report, PCT/JP2008/073577, Feb. 10, 2009.

*Primary Examiner* — Brian J Davis
(74) *Attorney, Agent, or Firm* — Young & Thompson

(57) ABSTRACT

A thermal recording material of the invention contains, as a storability improver, tris(2-methyl-4-hydroxy-5-t-butylphenyl)butane trapping and containing water and/or methanol and having a crystal structure that shows a maximum X-ray diffraction peak at a diffraction angle 2θ of 6.58° according to X-ray diffraction measurement using an X ray having a wavelength of a Cu—Kα line. The recording material has improved heat resistance in non-printing sections while maintaining the moisture-and-heat resistance in printing sections. The thermal recording material of the invention has a thermal-recording layer that contains the tris(2-methyl-4-hydroxy-5-t-butylphenyl)butane in an amount of preferably 0.1 to 15% by mass with respect to the thermal-recording layer. The amount of the water and/or methanol trapped and contained in the tris(2-methyl-4-hydroxy-5-t-butylphenyl)butane is preferably 0.1 to 10% by mass in total.

4 Claims, 2 Drawing Sheets

X-ray diffraction chart of Example 1-1(Crystal A)

X-ray diffraction chart of Example 1-2 (Crystal A')

X-ray diffraction chart of Comparative Example 1-1 (Crystal B)

X-ray diffraction chart of Comparative Example 1-2(Crystal C)

THERMAL RECORDING MATERIAL CONTAINING TRIS(2-METHYL-4-HYDROXY-5-T-BUTYLPHENYL)BUTANE

TECHNICAL FIELD

The present invention relates to a thermal recording material containing tris(2-methyl-4-hydroxy-5-t-butylphenyl)butane which traps and contains water and/or methanol.

BACKGROUND ART

Tris(2-methyl-4-hydroxy-5-t-butylphenyl)butane (also referred to hereinafter as "AO-30") is a compound widely used as an antioxidant for synthetic high-polymer materials such as polyolefins, ABS resin, and styrene-butadiene copolymers. Patent Document 1 proposes its usefulness as a storability improver in thermal recording paper. AO-30 with such great values is known to be produced, for example, through the reaction of 2-t-butyl-5-methylphenol and crotonaldehyde, as disclosed in Patent Document 2 listed below. Further, Patent Documents 3 to 5 describe that various types of crystals of AO-30, such as crystals having different crystal forms, crystals having a reduced organic solvent content, or hydrated crystals, can be produced by varying the recrystallization solvents and/or additives used during the production steps. Patent Documents 3 to 5 suggest the possibility of tackling problems arising during production, such as odor, flowability, and workability, as well as other problems such as foaming during mixing and coloring. These Patent Documents, however, describe nothing about using AO-30 for thermal recording materials.

It has long been considered that, in cases of using AO-30 as a storability improver for thermal recording paper, the use of materials having high melting points is effective in suppressing coloring of non-printing sections in the recording paper. For example, Patent Document 6 discloses a novel crystal having a high melting point which is described as improving the heat resistance of non-printing sections while maintaining the moisture-and-heat resistance of printing sections. Patent Document 6, however, does not completely solve the problem of background fogging. Accordingly, there still is a demand for further improvement in coloring suppressibility.

Patent Document 1: JP-A-58-57990
Patent Document 2: JP-B-39-4469
Patent Document 3: JP-A-56-40629
Patent Document 4: Specification of U.S. Pat. No. 4,467,119
Patent Document 5: JP-A-1-301634
Patent Document 6: Japanese Patent No. 3,816,132

DISCLOSURE OF INVENTION

Problems to be Solved by the Invention

An object of the present invention is to provide a thermal recording material, such as thermal recording paper, that has properties of enhancing color formation in printing sections while maintaining the moisture-and-heat resistance therein and that also has improved heat resistance in non-printing sections.

Means for Solving the Problems

Inventors have made elaborate investigation and have found that the heat resistance of non-printing sections on thermal recording paper can be improved by the use of crystals of AO-30 made to contain, by design, water and/or methanol.

Inventors have made further research on this type of AO-30 providing such favorable heat resistance, and found that this type of AO-30 has a lower melting point than that of AO-30 produced according to known methods. Furthermore, Inventors have found that this type of AO-30 shows a maximum X-ray diffraction peak at a diffraction angle 2θ of 6.58° according to X-ray diffraction measurement using an X ray having the wavelength of a Cu—Kα line, thus arriving at the present invention.

That is, the present invention provides a thermal recording material containing, as a storability improver, tris(2-methyl-4-hydroxy-5-t-butylphenyl)butane trapping and containing water and/or methanol and having a crystal structure that shows a maximum X-ray diffraction peak at a diffraction angle 2θ of 6.58° according to X-ray diffraction measurement using an X ray having a wavelength of a Cu—Kα line.

THE BEST MODE FOR CARRYING OUT THE INVENTION

Figure 1:
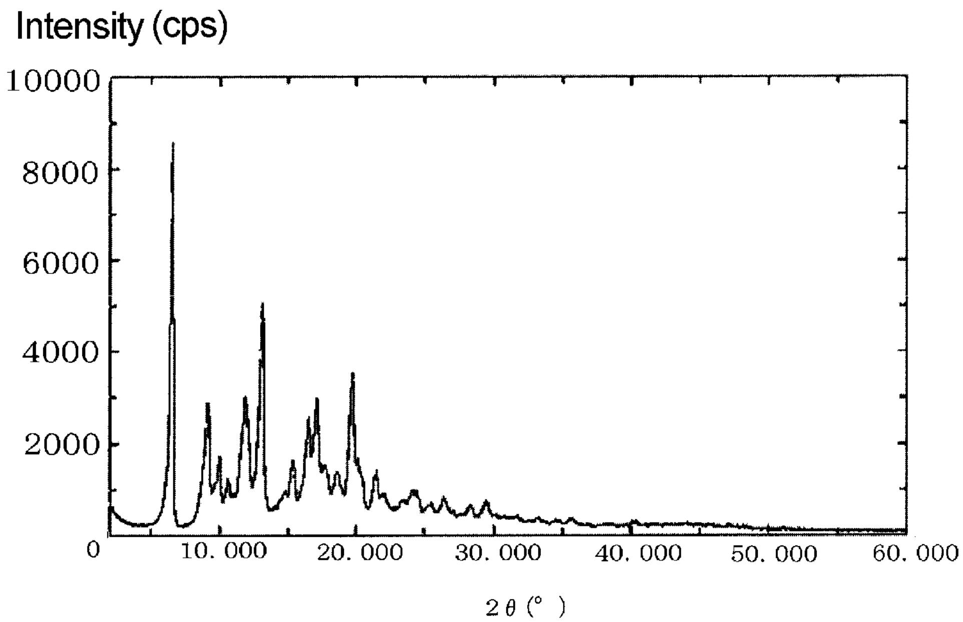
FIG. 1 shows an X-ray diffraction chart of AO-30 (Crystal A) according to the present invention obtained in Example 1-1.

A thermal recording material of the present invention containing a specific type of AO-30 (tris(2-methyl-4-hydroxy-5-t-butylphenyl)butane) as a storability improver is described in further detail below. Note that the AO-30 according to the present invention is 1,1,3-tris(2-methyl-4-hydroxy-5-t-butylphenyl)butane.

As mentioned above, the AO-30 crystal according to the present invention is a crystal of AO-30 which is in form of a clathrate with water and/or methanol and shows a maximum X-ray diffraction peak at a diffraction angle 2θ of 6.58° according to X-ray diffraction measurement using an X ray having a wavelength of a Cu—Kα line.

Because the AO-30 crystal according to the present invention traps and contains water and/or methanol, its melting point is lower than that of AO-30 having known crystal forms. The melting point of the AO-30 crystal according to the present invention, which can be determined from the DTA peak through TG/DTA measurement, is preferably 100 to 140° C., more preferably 110 to 140° C., and most preferably 113 to 135° C.

The AO-30 crystal according to the present invention can be prepared, for example, according to the following production method, although further details will be provided in the Examples described further below.

First, a crude-crystal solution of AO-30 is prepared according to ordinary methods. A recrystallization solvent is added to the crude-crystal solution, to thus obtain pure crystals of AO-30. Toluene is preferably used as the recrystallization solvent, but other solvents such as xylene, mesitylene, n-octane, or n-decane may be used instead.

Next, the pure crystals of AO-30 are dissolved into methanol to prepare a methanol solution, and the methanol solution is crystallized. The crystals that crystallize therefrom are the AO-30 crystals according to the present invention. In this step, adding water to crystallize the crystals from the methanol solution will allow a hydrated crystal—one of the AO-30 crystals of the present invention—to be prepared efficiently. It is preferable to use 200 to 1000 parts by mass of methanol with respect to 100 parts by mass of the above-mentioned pure crystals of AO-30. In cases of using water, the amount of water used is preferably 150 to 500 parts by mass with respect to 100 parts by mass of the above-mentioned pure crystals of AO-30.

The AO-30 crystals of the present invention prepared as above show a maximum X-ray diffraction peak at a diffraction angle 2θ of 6.58° according to X-ray diffraction measurement using an X ray having the wavelength of a Cu—Kα line, and have a melting point lower than that of AO-30 having known crystal forms. This will be described further below in the Examples.

The AO-30 crystals of the present invention may trap and contain only water, only methanol, or both water and methanol, as long as the crystals exhibit the above-mentioned X-ray diffraction peak. A crystal containing a larger amount of methanol has a higher melting point than a clathrate containing only water. The total amount of water and/or methanol trapped and contained in a molecule is preferably 0.1 to 10% by mass, more preferably 1.5 to 8.0% by mass, and most preferably 3.0 to 7.0% by mass.

The AO-30 crystal of the present invention, when added as a storability improver to a thermal recording material such as thermal recording paper, has the effect of improving the heat resistance of non-printing sections while maintaining the moisture-and-heat resistance of printing sections, as it will be described further below in the Examples.

The thermal recording material of the present invention is composed of a support and a thermal-recording layer. The present thermal recording material is similar to conventional ones, except that its thermal-recording layer contains the AO-30 crystal according to the present invention, and is thus not particularly limited in its usage, production method, etc.

The support to be used can appropriately be selected from, for example, paper, plastic, glass, or the like, depending on the use of the thermal recording material, and the thickness of the support is not particularly limited.

The thermal-recording layer is made of the AO-30 crystal according to the present invention, a developer, and a color former, and generally further includes a binder and a filler, and may also include, as necessary, storage stabilizers other than the AO-30 crystal of the present invention, sensitizers, light stabilizers, UV absorbers, pigments, metal soaps, hydrotalcites, plasticizers, amides, waxes, antioxidants, water resistance imparters, dispersing agents, antifoaming agents, surfactants, fluorescent dyes, antibacterial agents, antifungal agents, and antiseptics.

The content of the AO-30 of the present invention in the thermal-recording layer is preferably 0.1 to 15% by mass, and more preferably 1.0 to 5.0% by mass, with respect to the thermal-recording layer. If the content of AO-30 of the present invention is less than 0.1% by mass, no effect will be achieved by adding AO-30, whereas a usage amount of more than 15% by mass will only give rise to background fogging while hardly improving the storability of the printing sections.

In cases of combinedly using a storage stabilizer other than the AO-30 of the present invention, it is preferable that the total amount of all storage stabilizers in the thermal-recording layer is 0.1 to 15% by mass, and more preferably 1.0 to 5.0% by mass, from the same standpoint as above. In this case, the usage amount of storage stabilizer other than the AO-30 of the present invention should preferably be equal to or less than ten times, in mass, the usage amount of the AO-30 of the present invention.

Examples of the storage stabilizer other than the AO-30 of the present invention include: hindered phenol compounds such as 1,1,3-tris(2-methyl-4-hydroxy-5-cyclohexylphenyl) butane, 4,4'-butylidenebis(2-t-butyl-5-methylphenol), 4,4'-thiobis(2-t-butyl-5-methylphenol), 2,2'-thiobis(6-t-butyl-4-methylphenol), and 2,2'-methylene-bis(6-t-butyl-4-methylphenol); 4-benzyloxy-4'-(2-methylglycidyloxy) diphenyl sulfone; and sodium-2,2'-methylene-bis(4,6-di-t-butylphenyl)phosphate. A single type of the above stabilizer may be used, or two or more types may be used in combination.

Examples of the developer used in the thermal recording material of the present invention include: phenols such as p-octylphenol, p-t-butylphenol, p-phenylphenol, p-hydroxyacetophenone, α-naphthol, β-naphthol, p-t-octylcatechol, 2,2'-dihydroxybiphenyl, bisphenol A, 1,1-bis(p-hydroxyphenyl)butane, 2,2-bis(4-hydroxyphenyl)heptane, 2,2-bis-((3-methyl-4-hydroxyphenyl)propane), 2,2-bis-(3,5-dimethyl-4-hydroxyphenyl)propane, 2,2-bis(3,5-dichloro-4-hydroxyphenyl)propane, bis(4-hydroxyphenyl)sulfone, bis(3-allyl-4-hydroxyphenyl)sulfone, bis(3,4-dihydroxyphenyl)sulfone, 2,4'-dihydroxydiphenyl sulfone, 1,1-bis(4-hydroxyphenyl)cyclohexane, bis(4-hydroxyphenyl)ether, bis[2-(4-hydroxyphenylthio)ethoxy]methane, 4-(4-isopropoxyphenylsulfonyl)phenol, 4-(4-allyloxyphenylsulfonyl)phenol, 4-hydroxyphthalic acid dimethyl ester, bis(4-hydroxyphenyl)acetic acid butyl ester, p-hydroxybenzoic acid benzyl ester, 3,5-di-t-butylsalicylic acid, 2,4-dihydroxybenzanilide, 2,4-dihydroxy-2'-methoxybenzanilide, 2,4-dihydroxy-2',4'-dimethylbenzanilide, 2,4-dihydroxy-2'-methoxy-5'-methylbenzanilide, bis(4-(2,4-dihydroxyphenylcarbonylamino)-3-methoxyphenyl)methane, 4-methylbenzene sulfonic acid-2-hydroxyanilide, ester compounds of (poly)-4-hydroxybenzoic acid and a polyol having a valence of three or higher, and compounds disclosed in JP-A-11-322727; phenolic resins such as novolac phenol; sulfone amides such as compounds disclosed in JP-A-11-286175; phosphoric amides such as compounds disclosed in JP-A-2007-196631; resorcinols; organic carboxylic acids such as benzoic acid; metal salts such as zinc salicylate; N,N-diarylthiourea derivatives; sulfonylurea derivatives; and urethane urea compounds. A single type of the above developer may be used, or two or more types may be used in combination.

Among the above developers, sulfonylphenols such as 4-(4-isopropoxyphenylsulfonyl)phenol and 4-(4-allyloxyphenylsulfonyl)phenol are preferable because they significantly bring out the effect of the AO-30, which is the storability improver of the present invention.

The amount of developer to be added is preferably 20 to 80% by mass, and more preferably 30 to 70% by mass, with respect to the thermal-recording layer.

Examples of the color former that may be used in the thermal-recording layer in the thermal recording material of the present invention include various known dyes that are colorless or light-colored under normal conditions, and any color former used in generally-used thermal recording materials etc. may be employed without particular limitation. Concrete examples of the color former include: (i) triarylmethane-based compounds such as 3,3-bis(p-dimethylaminophenyl)-6-dimethylaminophthalide, 3-(p-dimethylaminophenyl)-3-(2-phenyl-3-indolyl)phthalide, 3-(p-dimethylaminophenyl)-3-(1,2-dimethyl-3-indolyl)phthalide, 3,3-bis(9-ethyl-3-carbazolyl)-5-dimethylaminophthalide, 3,3-bis(2-phenyl-3-indolyl)-5-dimethylaminophthalide, 3-(4-diethylaminophenyl)-3-(1-ethyl-2-methylindol-3-yl)phthalide, and 3,3-bis[2-(4-dimethylaminophenyl)-2-(4-methoxyphenyl)vinyl]-4,5,6,7-tetrachlorophthalide; (ii) diphenylmethane-based compounds such as 4,4-bis(dimethylamino)benzhydrin benzyl ether and N-2,4,5-trichlorophenyl leucoauramine; (iii) xanthene-based compounds such as rhodamine-β-anilinolactam, 3-(N-methyl-N-cyclohexylamino)-6-methyl-7-anilinofluoran, 3-diethylamino-7-octylaminofluoran, 3-diethylamino-7-(2-chloroanilino)fluoran, 3-diethylamino-7-(2-fluoroanilino)fluoran, 3-diethylamino-6-methyl-7-anilinofluoran, 3-diethylamino-6-methyl-7-(2,4-dimethylanilino)fluoran, 3-diethylamino-7-dibenzylaminofluoran, 3-diethylamino-6-chloro-7-(β-ethoxyethylamino)fluoran, 3-diethylamino-6-chloro-7-(γ-chloropropylamino)fluoran, 3-(N-ethyl-N-isoamylamino)-6-methyl-7-anilinofluoran, 3-(N-ethyl-N-ethoxyethylamino)-6-methyl-7-anilinofluoran, 3-(N-ethyl-N-tetrahydrofurfuryl amino)-6-methyl-7-anilinofluoran, 3-dibutylamino-7-(2-chloroanilino)fluoran, 3-(N-ethyl-N-tolylamino)-6-methyl-7-anilinofluoran, 3-(N,N-dibutylamino)-6-methyl-7-anilinofluoran, 3-dipentylamino-6-methyl-7-anilinofluoran, 3-piperidino-6-methyl-7-anilinofluoran, and 3-(4-anilino)anilino-6-methyl-7-chlorofluoran; (iv) thiazine-based compounds such as benzoylleucomethylene blue and p-nitrobenzoylleucomethylene blue; (v) spiro compounds such as 3-methylspirodinaphthopyran, 3-ethylspirodinaphthopyran, 3-benzylspirodinaphthopyran, 3-methylnaphtho-(3-methoxybenzo)spiropyran, and 3-propylspirodibenzopyran; and (vi) other compounds such as 3,5',6-tris(dimethylamino)-spiro[9H-fluorene-9,1'-(3'H)-isobenzofuran]-3'-one, 1,1-bis[2-(4-dimethylaminophenyl)-2-(4-methoxyphenyl)ethenyl]-4,5,6,7-tetrachloro(3H)isobenzofuran-3-one, 3-(4-diethylamino-2-ethoxyphenyl)-3-(1-ethyl-2-methylindol-3-yl)-4-azaphthalide, 3-(4-diethylamino-2-methylphenyl)-3-(1-ethyl-2-methylindol-3-yl)-4-azaphthalide, and phenoxazine derivatives. Several types of these dyes may be used mixed.

Among the above examples given in (i) to (vi), 3-(N,N-dibutylamino)-6-methyl-7-anilinofluoran and 3-(N-ethyl-N-isoamylamino)-6-methyl-7-anilinofluoran are used preferably. Further, the thermal recording material of the present invention may combinedly use, as necessary, chelate color formers such as ferric salts of fatty acids.

The amount of color former to be used is preferably 0.1 to 80% by mass, and more preferably 20 to 40% by mass, with respect to the thermal-recording layer.

Examples of the sensitizer used as necessary include: metal salts of organic acids, such as zinc acetate, zinc octylate, zinc laurate, zinc stearate, zinc oleate, zinc behenate, zinc benzoate, a zinc salt of salicylic acid dodecyl ester, calcium stearate, magnesium stearate, and aluminum stearate; amide compounds such as stearamide, behenamide, stearic methylol amide, stearoyl urea, acetanilide, acetotoluidide, acetoacetanilide, acetoacetic-o-chloroanilide, benzoylacetanilide, benzoic acid stearyl amide, ethylene bis stearamide, and hexamethylene bis octylic amide; and other compounds such as 1,2-bis(3,4-dimethylphenyl)ethane, m-terphenyl, 1,2-diphenoxyethane, 1,2-bis(3-methylphenoxy)ethane, p-benzylbiphenyl, p-benzyloxybiphenyl, diphenyl carbonate, bis(4-methylphenyl)carbonate, dibenzyl oxalate, bis(4-methylbenzyl) oxalate, bis(4-chlorobenzyl)oxalate, 1-hydroxy-2-naphthalenecarboxylic acid phenyl ester, 1-hydroxy-2-naphthalenecarboxylic acid benzyl ester, 3-hydroxy-2-naphthalenecarboxylic acid phenyl ester, methylene benzoate, 1,4-bis(2-vinyloxyethoxy)benzene, 2-benzyloxynaphthalene, 4-benzyloxybenzoic acid benzyl ester, dimethyl phthalate, terephthalic acid dibenzyl ester, dibenzoylmethane, diphenylsulfone, p-toluenesulfonic acid anilide, 4-methylphenoxy-p-biphenyl, and 4-chlorophenylphenylsulfone. A single type of the above sensitizer may be used, or two or more types may be used in combination. Among the above, in particular, bis(4-methylbenzyl) oxalate, bis(4-chlorobenzyl) oxalate, acetoacetic-o-chloroanilide, diphenylsulfone, stearamide, stearic methylol amide, or ester compounds of terephthalic acid may preferably be used.

In case of adding the sensitizer, the amount to be added is preferably 0.1 to 80% by mass, and more preferably 20 to 50% by mass, with respect to the thermal-recording layer. The sensitizer, if employed as an ingredient, may be used separately from the other ingredients, but it may be molten and mixed with a developer in advance and used in this form as an ingredient.

The developer, the color former, and the sensitizer used in the thermal recording material of the present invention are usually made into a coating fluid by being granulated—along with other ingredients, such as the storage stabilizer including the AO-30 of the present invention—using a grinder such as a ball mill, an attritor, or a sand grinder, or an appropriate emulsifying device, and then being mixed with various other additives depending on the purpose thereof.

The coating fluid usually contains, as the binder, polyvinyl alcohol, hydroxyethylcellulose, methylcellulose, polyvinyl pyrrolidone, polyacrylamide, starches, styrene-maleic anhydride copolymer, vinyl acetate-maleic anhydride copolymer, styrene-butadiene copolymer, or a modified compound of the above. The coating fluid also usually contains, as the filler, kaoline, silica, diatomite, talc, titanium dioxide, calcium carbonate, magnesium carbonate, aluminum hydroxide, melamine, or the like. The coating fluid may further contain, as necessary, the above-mentioned metal soaps, amides, waxes, light stabilizers, water resistance imparters, dispersing agents, antifoaming agents, and other additives.

The thermal recording material of the present invention may also be provided with an overcoat layer on the surface of the thermal-recording layer with the aim of imparting further improved storage stability, as well as an undercoat layer with the aim of further improving the sensitivity to color formation.

The overcoat layer may be formed, for example, by applying a photocurable resin, an electron-beam-curable resin, or a heat-curable resin and curing the resin into a film. Instead, a film may be formed by combinedly using a cross-linking agent or a curing agent, such as an epoxy compound, at the time of coating a film-formable latex or water-soluble polymer to form the film. Any known method may be employed for the coating process, and there is also no limitation to the thickness of the overcoat layer. The method/thickness may be chosen as appropriate to achieve the desired properties.

As for the undercoat layer, it is possible to use, for example, materials exhibiting good heat insulation, such as a layer containing an inorganic and/or organic pigment and an adhesive as its main components, a layer containing a foaming filler and an adhesive as its main components, a layer containing granular and/or fibrous inorganic and/or organic hollow materials and an adhesive as its main components, and/or a foam layer made of a coating fluid obtained by mechanically foaming an aqueous solution containing a water-soluble or water-dispersible polymer compound. Using such materials can achieve color formation with a small amount of energy. Also for the undercoat layer, the coating method and the layer thickness are not particularly limited and may be chosen as appropriate to achieve the desired properties.

In cases where a particularly high degree of lightfastness and storage stability of the background sections is required of the thermal recording material, one type, or two or more types, of known hindered amine-based light stabilizers and/or UV absorbers may be added to the thermal-recording layer and/or the overcoat layer.

Examples of the hindered amine-based light stabilizers include: 2,2,6,6-tetramethyl-4-piperidyl benzoate, N-(2,2,6,6-tetramethyl-4-piperidyl)dodecylsuccinimide, 1-[(3,5-di-t-butyl-4-hydroxyphenyl)propionyloxyethyl]-2,2,6,6-tetramethyl-4-piperidyl-(3,5-di-t-butyl-4-hydroxyphenyl) propionate, bis(2,2,6,6-tetramethyl-4-piperidyl)sebacate, bis(1,2,2,6,6-pentamethyl-4-piperidyl)sebacate, bis(1,2,2,6,6-pentamethyl-4-piperidyl)-2-butyl-2-(3,5-di-t-butyl-4-hydroxybenzyl)malonate, N,N-bis(2,2,6,6-tetramethyl-4-piperidyl)hexamethylenediamine, tetra(2,2,6,6-tetramethyl-4-piperidyl)butane tetracarboxylate, tetra(1,2,2,6,6-pentamethyl-4-piperidyl)butane tetracarboxylate, bis(2,2,6,6-tetramethyl-4-piperidyl).di(tridecyl)butane tetracarboxylate, bis(1,2,2,6,6-pentamethyl-4-piperidyl).di(tridecyl)butane tetracarboxylate, 3,9-bis[1,1-dimethyl-2-{tris(2,2,6,6-tetramethyl-4-piperidyloxycarbonyloxy) butylcarbonyloxy}ethyl]-2,4,8,10-tetraoxaspiro[5.5] undecane, 3,9-bis[1,1-dimethyl-2-{tris(1,2,2,6,6-pentamethyl-4-piperidyloxycarbonyloxy) butylcarbonyloxy}ethyl]-2,4,8,10-tetraoxaspiro[5.5] undecane, 1,5,8,12-tetrakis[4,6-bis{N-(2,2,6,6-tetramethyl-4-piperidyl)butylamino}-1,3,5-triazin-2-yl]-1,5,8,12-tetraazadodecane, 1-(2-hydroxyethyl)-2,2,6,6-tetramethyl-4-piperidinol/dimethyl succinate condensate, 2-t-octylamino-4,6-dicyclo-s-triazine/N,N-bis(2,2,6,6-tetramethyl-4-piperidyl)hexamethylenediamine condensate, and N,N'-bis(2,2,6,6-tetramethyl-4-piperidyl)hexamethylenediamine/dibromoethane condensate.

Examples of the UV absorbers include: 2-hydroxybenzophenones such as 2,4-dihydroxybenzophenone, 2-hydroxy-4-methoxybenzophenone, 2-hydroxy-4-octoxybenzophenone, and 5,5'-methylene-bis(2-hydroxy-4-methoxybenzophenone); 2-(2-hydroxyphenyl) benzotriazoles such as 2-(2-hydroxy-5-methylphenyl) benzotriazole, 2-(2-hydroxy-5-t-octylphenyl)benzotriazole, 2-(2-hydroxy-3,5-di-t-butylphenyl)-5-chlorobenzo triazole, 2-(2-hydroxy-3-t-butyl-5-methylphenyl)-5-chlorobenzotriazole, 2-(2-hydroxy-3,5-dicumylphenyl)benzotriazole, 2,2'-methylene-bis(4-t-octyl-6-benzotriazolylphenol), a polyethylene glycol ester of 2-(2-hydroxy-3-t-butyl-5-carboxyphenyl)benzotriazole, 2-[2-hydroxy-3-(2-acryloyloxyethyl)-5-methylphenyl]benzotriazole, 2-[2-hydroxy-3-(2-methacryloyloxyethyl)-5-t-butylphenyl] benzotriazole, 2-[2-hydroxy-3-(2-methacryloyl oxyethyl)-5-t-octylphenyl]benzotriazole, 2-[2-hydroxy-3-(2-methacryloyloxyethyl)-5-t-butylphenyl]-5-chlorobenzotriazole, 2-[2-hydroxy-5-(2-methacryloyloxyethyl)phenyl]benzotriazole, 2-[2-hydroxy-3-t-butyl-5-(2-methacryloyloxyethyl)phenyl]benzotriazole, 2-[2-hydroxy-3-t-amyl-5-(2-methacryloyloxyethyl)phenyl] benzotriazole, 2-[2-hydroxy-3-t-butyl-5-(3-methacryloyloxypropyl)phenyl]-5-chlorobenzotriazole, 2-[2-hydroxy-4-(2-methacryloyloxymethyl)phenyl]benzotriazole, 2-[2-hydroxy-4-(3-methacryloyloxy-2-hydroxypropyl)phenyl] benzotriazole, and 2-[2-hydroxy-4-(3-methacryloyloxypropyl)phenyl]benzotriazole; 2-(2-hydroxyphenyl)-4,6-diaryl-1,3,5-triazines such as 2-(2-hydroxy-4-methoxyphenyl)-4,6-diphenyl-1,3,5-triazine, 2-(2-hydroxy-4-hexyloxy phenyl)-4,6-diphenyl-1,3,5-triazine, 2-(2-hydroxy-4-octoxyphenyl)-4,6-bis(2,4-dimethyl phenyl)-1,3,5-triazine, 2-[2-hydroxy-4-(3-alkoxy (C12 to C13 mixture)-2-hydroxypropoxy)phenyl]-4,6-bis(2,4-dimethylphenyl)-1,3,5-triazine, 2-[2-hydroxy-4-(2-acryloyloxyethoxy)phenyl]-4,6-bis(4-methylphenyl)-1,3,5-triazine, 2-(2,4-dihydroxy-3-allylphenyl)-4,6-bis(2,4-dimethylphenyl)-1,3,5-triazine, and 2,4,6-tris(2-hydroxy-3-methyl-4-hexyloxyphenyl)-1,3,5-triazine; benzoates such as phenyl salicylate, resorcinol monobenzoate, 2,4-di-t-butylphenyl-3,5-di-t-butyl-4-hydroxy benzoate, and hexadecyl-3,5-di-t-butyl-4-hydroxy benzoate; substituted oxanilides such as 2-ethyl-2'-ethoxyoxanilide and 2-ethoxy-4'-dodecyloxanilide; cyano acrylates such as ethyl-α-cyano-β,β-diphenyl acrylate and methyl-2-cyano-3-methyl-3-(p-methoxyphenyl)acrylate; and various metal salts or metal chelates. Among the above, in particular, salts or chelates of nickel or chromium and 2-(2-hydroxyphenyl)benzotriazoles are preferred.

The amount of light stabilizer(s) and UV absorber(s) to be added is preferably 0.01 to 10 parts by mass, and more preferably 0.05 to 5 parts by mass, with respect to 1 part by mass of the developer. An amount less than 0.01 parts by mass may not achieve a sufficient stabilizing effect, whereas a usage amount of more than 10 parts by mass is not only useless and wasteful but may also negatively affect the physical properties of the coating/film.

The thermal recording material of the present invention may be used in various applications where thermal recording materials may be employed, such as for: recording paper used in various measuring instruments, computers, facsimile machines, telex teleprinters, etc.; boarding tickets, prepaid cards, etc. that are thermally recorded by automatic ticket-vending machines etc.; and other sheets such as labels and register receipts.

EXAMPLES

The present invention will be described in further detail below according to Examples and Comparative Examples. The present invention, however, is not to be limited whatsoever to these Examples etc.

Examples 1-1 and 1-2 and Comparative Examples 1-1 and 1-2 are examples of producing various types of AO-30. The various types of AO-30 obtained were analyzed through X-ray diffraction analysis etc. The analyses results provide evidence that the crystal form of the AO-30 of the present invention is novel.

Example 2-1 and Comparative Examples 2-1 to 2-3 provide a working example and comparative examples of thermal recording paper serving as thermal recording materials.

Example 1-1

To 300 ml of methanol were dissolved 492 g (3 mol) of 2-t-butyl-5-methylphenol and 175 ml (2 mol) of concentrated hydrochloric acid, and while stirring the mixture and bringing it to reflux, 70 g (1 mol) of crotonaldehyde was added thereto dropwise in 1 hour. The mixture was allowed to react under reflux for 1 hour and was then neutralized with a sodium carbonate aqueous solution, to obtain a crude AO-30 solution. To the obtained crude AO-30 solution was added 1500 g of toluene, and the solution was heated to 115° C. and kept in that state for 30 minutes to remove methanol and water. The solution was cooled for precipitation, and the precipitate was filtered off, was washed with toluene and water, and was heated to dry under a reduced pressure, to obtain 446 g of a white powder (referred to hereinafter as "Crystal B") having a melting point of 187° C. (yield: 82%).

Into a 3-L reaction flask were placed 400 g of the obtained Crystal B and 1,600 g of methanol, and the mixture was heated to 60° C. to allow the crystal to dissolve. To this solution, 800 g of ion exchanged water was added dropwise in approximately 1 hour, to allow the solution to crystallize. The mixture was allowed to cool to room temperature. Then, the crystal was filtered by suction, and the obtained white powder was washed on the funnel using 1,600 g of ion exchanged water and was then dried under vacuum at 60° C. for 4 hours using a rotary evaporator, to obtain 394 g of a white powder (referred to hereinafter as "Crystal A") (yield: 98.5%). The obtained Crystal A was subjected to various analyses described below.

Example 1-2

Into a 2-L reaction flask were placed 200 g of the Crystal B obtained in Example 1-1 and 850 g of methanol, and the mixture was heated to 60° C. to allow the crystal to dissolve. The solution was continuously heated to 65° C. to remove 600 g of the methanol by evaporation. After removal, the solution was cooled to room temperature for crystallization, and the obtained crystal was filtered off and was dried under vacuum at 60° C. for 4 hours, to obtain 140 g of a white powder (referred to hereinafter as "Crystal A'") (yield: 70.0%). The obtained Crystal A' was subjected to various analyses described below.

Moisture meter: "MOISTURE CA-06" manufactured by Mitsubishi Chemical Corporation (Anolyte: "ACROMICRON AKX" manufactured by Mitsubishi Chemical Corporation)

(Catholyte: "ACROMICRON CXU" manufactured by Mitsubishi Chemical Corporation)

X-ray diffraction: "Ultima+" manufactured by Rigaku Corporation

The results of $^1$H-NMR spectroscopy (solvent: DMSO-d$^6$) showed no difference among the respective $^1$H-NMR spectra of Crystal A, Crystal A', Crystal B, and Crystal C, except for the solvents contained.

The results of TG/DTA measurement and moisture measurement for Crystal A, Crystal A', Crystal B, and Crystal C are shown in Table 1 below. In Table 1, the "melting point" of each sample is a value read off from the bottom peak in DTA measured with a TG/DTA measurement device by raising the temperature at a rate of 10° C. per minute using alumina as the reference, and the "weight reduction" is a value obtained from the reduction in weight when the temperature was raised up to 250° C. during TG/DTA measurement.

Table 1 below reveals that both Crystals A and A' showed a larger weight reduction compared to Crystal C but not much difference in weight reduction compared to Crystal B, but both Crystals A and A' had lower melting points than the known Crystals B and C. Further, both Crystals A and A' (particularly Crystal A) contained more water compared to Crystals B and C.

TABLE 1

| | Example 1-1 (Crystal A) | Example 1-2 (Crystal A') | Comparative Example 1-1 (Crystal B) | Comparative Example 1-2 (Crystal C) |
|---|---|---|---|---|
| Weight reduction while reaching 250° C. (%) | 4.6 | 5.5 | 4.1 | 0.6 |
| Melting point (° C.) | 115.6 | 131.3 | 187.4 | 203.3 |
| Moisture amount (%) | 6.6 | 1.6 | 0.1 | 0.1 |

Comparative Example 1-1

The Crystal B obtained in Example 1-1 above was used as-is and was subjected to various analyses described below.

Comparative Example 1-2

The toluene, which was used as the recrystallization solvent for obtaining the Crystal B in Example 1-1, was replaced by a Stoddard solvent (aromatic/aliphatic-mixed hydrocarbon solvent manufactured by Chinese Petroleum Corporation (Taiwan)), but except for this, the same procedure as that in Example 1-1 was followed, to obtain 462 g of a white powder (referred to hereinafter as "Crystal C") (yield: 85%). The obtained Crystal C was subjected to various analyses described below.

Various Analyses

Crystal A, Crystal A', Crystal B, and Crystal C obtained as above were subjected to TG/DTA measurement, $^1$H-NMR spectroscopy, moisture measurement, and X-ray diffraction analysis. The instruments used for measurement were as follows.

TG/DTA: "EXSTAR TG/DTA 6200" manufactured by Seiko Instruments Inc.

$^1$H-NMR: "ECA400" manufactured by JEOL Ltd.

Figure 2:
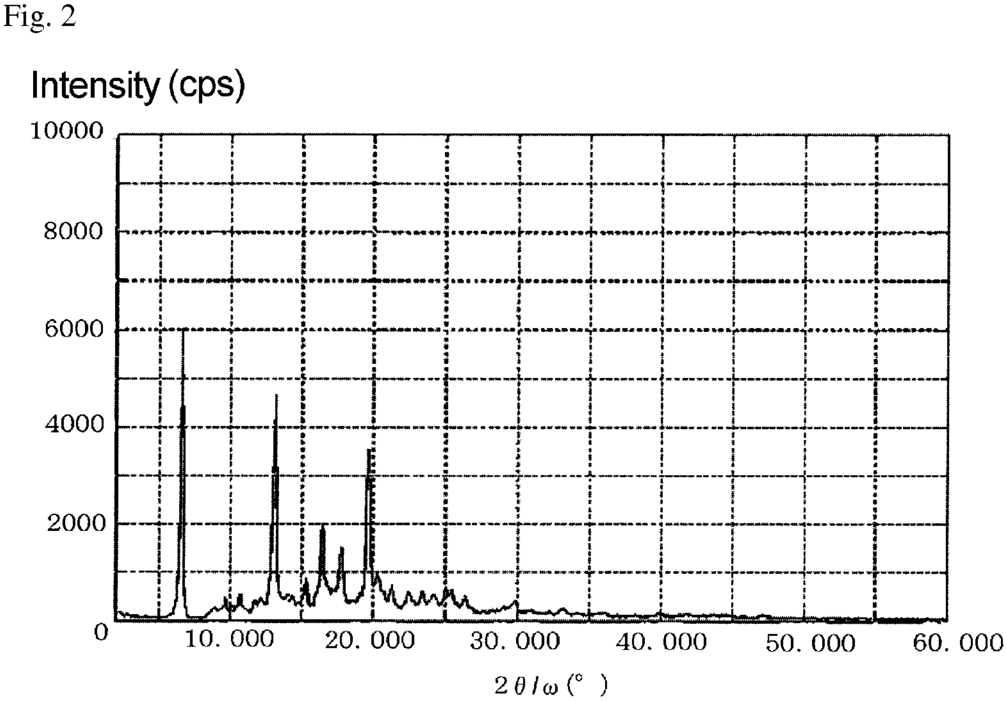
FIG. 2 shows an X-ray diffraction chart of AO-30 (Crystal A') according to the present invention obtained in Example 1-2.
Figure 3:
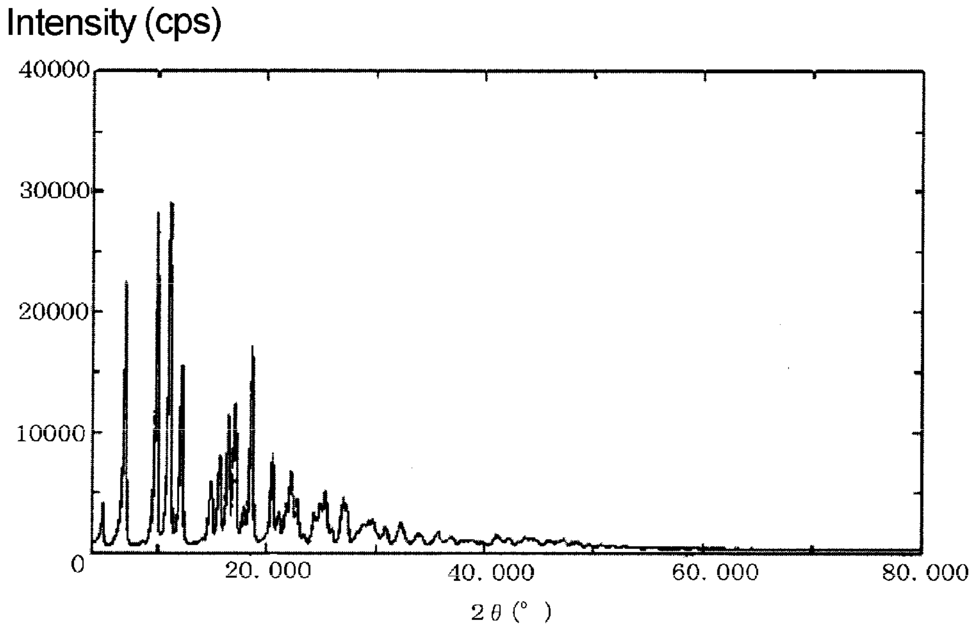
FIG. 3 shows an X-ray diffraction chart of AO-30 (Crystal B) of Comparative Example 1-1.
Figure 4:
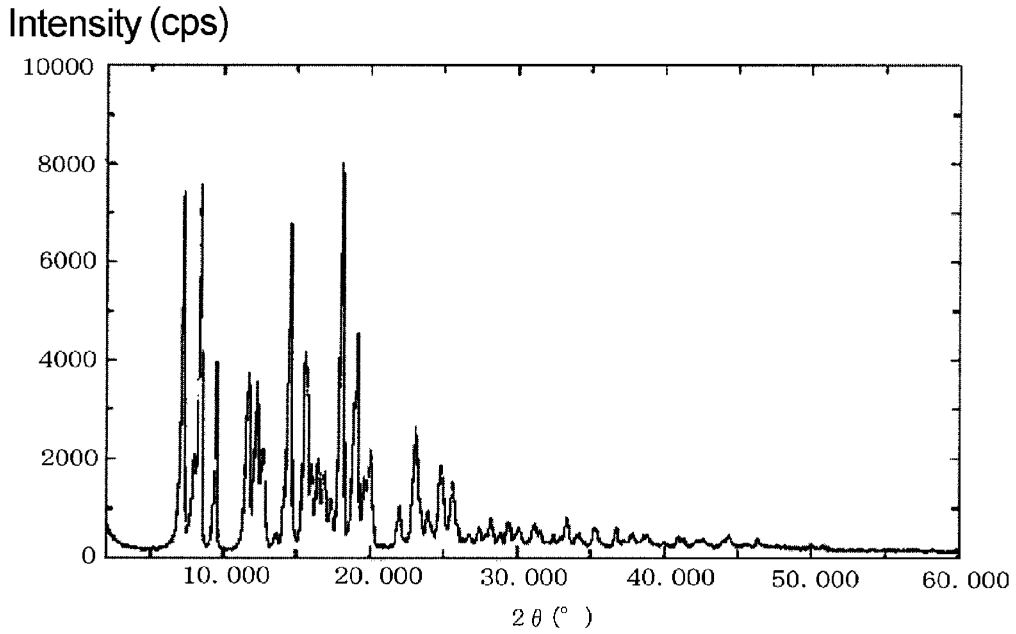
FIG. 4 shows an X-ray diffraction chart of AO-30 (Crystal C) of Comparative Example 1-2.

Further, the X-ray diffraction peaks of the Crystals A, A', B, and C found through X-ray diffraction analysis with an X ray having a wavelength of a Cu—Kα line are respectively shown in the charts given in FIGS. 1 to 4. (The horizontal axis in each chart indicates the diffraction angle 2θ (°).) The numerical data of the X-ray diffraction peaks seen in the Figures are shown in Table 2 below. Note that Table 2 shows the relative intensity for each X-ray diffraction peak when the maximum peak intensity for each spectrum is regarded as 100.

The X-ray diffraction measurement conditions were as follows:

X-ray Diffraction Measurement Conditions

Conditions for Analyzing X-ray Diffraction:

X Ray: Cu—Kα

Tube voltage/Tube current: 40 kV/40 mA

Goniometer: Horizontal goniometer ("Ultima+")

Attachment: Standard sample holder

Filter: Not used

Incident monochrome: Not used

Counter monochromator: Fixed monochromator

Divergence slit: ½°

Soller slit: 10 mm

Scatter slit: 0.73 mm

Receiving slit: 0.3 mm
Monochrome receiving slit: None
Counter: Scintillation counter
Scanning mode: Continuous
Scanning speed: 4.000°/min
Sampling width: 0.020°
Scanning axis: 2θ/θ
Scanning range: 2.000 to 60.000 (or 2.000 to 80.000)
θ offset: 0.000

TABLE 2

| Ex. 1-1 (Crystal A) | | Ex. 1-2 (Crystal A') | | Comp. Ex. 1-1 (Crystal B) | | Comp. Ex. 1-2 (Crystal C) | | | |
|---|---|---|---|---|---|---|---|---|---|
| 2θ (°) | relative intensity | 2θ (°) | relative intensity | 2θ (°) | relative intensity | 2θ (°) | relative intensity | 2θ (°) | relative intensity |
| 6.08 | 14 | 6.58 | 100 | 5.02 | 15 | 7.10 | 45 | 16.82 | 21 |
| 6.58 | 100 | 10.66 | 10 | 6.58 | 14 | 7.30 | 93 | 17.36 | 16 |
| 8.62 | 13 | 13.08 | 73 | 7.08 | 79 | 7.96 | 25 | 17.90 | 44 |
| 8.82 | 19 | 13.14 | 78 | 9.72 | 34 | 8.02 | 27 | 17.98 | 61 |
| 9.12 | 34 | 13.40 | 11 | 9.98 | 100 | 8.08 | 24 | 18.06 | 85 |
| 9.20 | 32 | 15.28 | 15 | 11.20 | 100 | 8.38 | 67 | 18.12 | 100 |
| 10.04 | 20 | 16.44 | 34 | 12.22 | 55 | 8.48 | 94 | 18.72 | 20 |
| 10.56 | 15 | 16.76 | 14 | 14.92 | 22 | 9.56 | 49 | 19.00 | 42 |
| 10.66 | 15 | 16.90 | 12 | 15.04 | 17 | 11.56 | 34 | 19.16 | 57 |
| 11.38 | 15 | 17.16 | 12 | 15.78 | 29 | 11.66 | 42 | 19.50 | 16 |
| 11.52 | 21 | 17.34 | 11 | 16.56 | 40 | 11.78 | 47 | 19.58 | 21 |
| 11.64 | 28 | 17.48 | 12 | 17.04 | 36 | 12.10 | 28 | 19.68 | 20 |
| 11.88 | 36 | 17.80 | 26 | 17.20 | 43 | 12.30 | 45 | 19.76 | 19 |
| 11.96 | 34 | 17.92 | 23 | 17.98 | 14 | 12.36 | 42 | 19.86 | 21 |
| 12.14 | 26 | 19.74 | 57 | 18.70 | 61 | 12.54 | 20 | 20.00 | 27 |
| 12.50 | 14 | 20.24 | 16 | 20.62 | 29 | 12.64 | 25 | 20.06 | 26 |
| 12.78 | 26 | 20.32 | 17 | 21.88 | 15 | 12.80 | 25 | 23.18 | 27 |
| 13.14 | 60 | 20.42 | 15 | 22.26 | 24 | 14.10 | 14 | 23.40 | 15 |
| 15.38 | 20 | 20.76 | 11 | 22.38 | 20 | 14.38 | 39 | 24.74 | 22 |
| 16.24 | 20 | 21.24 | 12 | 22.88 | 16 | 14.50 | 57 | 24.84 | 24 |
| 16.52 | 31 | 21.32 | 13 | 24.42 | 13 | 14.64 | 85 | 24.92 | 21 |
| 16.88 | 26 | 24.98 | 12 | 24.96 | 15 | 15.38 | 17 | 25.02 | 16 |
| 17.14 | 35 | 25.36 | 10 | 25.02 | 15 | 15.58 | 53 | 25.44 | 15 |
| 17.44 | 17 | 25.48 | 11 | 25.46 | 19 | 15.76 | 41 | 25.54 | 19 |
| 17.66 | 19 | | | 27.04 | 14 | 15.96 | 20 | 25.66 | 18 |
| 17.78 | 19 | | | 27.14 | 16 | 16.04 | 24 | | |
| 17.96 | 16 | | | 27.42 | 15 | 16.06 | 24 | | |
| 18.48 | 16 | | | | | 16.40 | 23 | | |
| 18.70 | 16 | | | | | 16.50 | 25 | | |
| 19.58 | 34 | | | | | 16.62 | 17 | | |

FIGS. 1 to 4 and Table 2 reveal that AO-30 having the structure of Crystal A or Crystal A' shows a maximum X-ray diffraction peak at a diffraction angle 2θ of 6.58° according to the above-mentioned X-ray diffraction measurement, whereas Crystal B shows maximum X-ray diffraction peaks at diffraction angles 2θ of 9.98° and 11.20° and Crystal C shows a maximum X-ray diffraction peak at a diffraction angle 2θ of 18.12°. These results show that the AO-30 crystals having the structure of Crystal A and Crystal A' have crystal forms that differ from Crystal B and Crystal C that have been used as known storability improvers.

Example 2-1 and Comparative Examples 2-1 to 2-3

Sheets of thermal recording paper were prepared and evaluated according to the following procedures. Note that in the following description, "%" indicates "% by weight".

Preparing 10% PVA Solution

To a 2000-ml beaker was placed 900 g of water. The water was heated to approximately 60° C., and while keeping the water at that temperature and stirring it, a total of 100 g of "KURARAY POVAL PVA405" (polyvinyl alcohol manufactured by Kuraray Co., Ltd.) was dissolved slowly thereto, to prepare a 10% PVA solution.

Preparing Developer Dispersion Liquid

To a 100-ml narrow-mouthed plastic bottle were placed 2 g of the 10% PVA aqueous solution, 0.2 g of a 10% aqueous solution of "PELEX SSH" manufactured by Kao Corporation, 8.3 g of water, 2.0 g of 4-(4-isopropoxyphenylsulfonyl) phenol as a developer, and 20 g of glass beads (average particle size: 0.177 to 0.250), and the mixture was shaken for 12 hours on a "THERMO-SHAKER MODEL Z-1" manufactured by Thermonics Co., Ltd. at Speed 3.5, to prepare a developer dispersion liquid.

Preparing Storability Improver Dispersion Liquid

To a 100-ml narrow-mouthed plastic bottle were placed 2 g of the 10% PVA aqueous solution, 0.2 g of a 10% aqueous solution of "PELEX SSH" manufactured by Kao Corporation, 8.3 g of water, 2.0 g of 1,1,3-tris(2-methyl-4-hydroxy-5-t-butylphenyl)butane (as specified in Tables 3 and 4) as a storability improver, and 20 g of glass beads (average particle size: 0.177 to 0.250), and the mixture was shaken for 12 hours on a "THERMO-SHAKER MODEL Z-1" manufactured by Thermonics Co., Ltd. at Speed 3.5, to prepare each storability improver dispersion liquid.

Preparing Dye Dispersion Liquid

To a 100-ml narrow-mouthed plastic bottle were placed 2 g of the 10% PVA solution, 0.02 g of "EPAN 420" manufactured by Dai-Ichi Kogyo Seiyaku Co., Ltd., 8.48 g of water, 2.0 g of 3-dibutylamino-6-methyl-7-anilinofluoran as a dye (color former), and 20 g of glass beads (average particle size:

0.177 to 0.250), and the mixture was shaken for 12 hours on a "THERMO-SHAKER MODEL Z-1" manufactured by Thermonics Co., Ltd. at Speed 3.5, to prepare a dye dispersion liquid.

Preparing Coating Fluid

In a No. 2 screw-cap bottle (6 cc) were measured 1 g of the dye dispersion liquid, 2 g of the developer dispersion liquid, and 0.2 g of one of the storability improver dispersion liquids, all prepared as above. The mixture was stirred for about 1 hour and was then left still until the bubbles disappeared, to thus prepare each coating fluid.

Preparation and Evaluation of Thermal Recording Paper

Each coating fluid was coated on base paper to a thickness of 32 μm using a bar coater and was allowed to dry, to thus prepare each sheet of thermal recording paper. Printing was performed on each sheet of thermal recording paper at 220° C. using a static color formation tester manufactured by Okura Engineering Co., Ltd., to thus prepare each evaluation specimen. The densities of the printing section and the non-printing section of each evaluation specimen were measured with a Macbeth densitometer ("Model RD-933" manufactured by Macbeth). The evaluation specimens were stored according to the following heat resistance storage test conditions and moisture-and-heat resistance storage test conditions, and after storage, the densities of the printing section and the non-printing section were again measured. Table 3 shows the measurement results for the printing sections, and Table 4 shows the measurement results for the non-printing sections.

Heat Resistance Storage Test Conditions:

Stored for 2 hours in dry atmosphere at 80° C. or 100° C. using "EYRLA WFO-400" manufactured by Tokyo Rikakikai Co., Ltd.

Moisture-and-Heat Resistance Storage Test Conditions:

Stored for 1 hour at 60° C. and 90% RH using "Compact Environmental Test Chamber JUINOR Series SD-01" manufactured by Kusumoto Chemicals, Ltd.

TABLE 3

| | | | Moisture-and-heat resistance (density) | |
|---|---|---|---|---|
| | Storability improver | Area measured | Initial | Stored for 1 h at 60° C., 90% |
| Example 2-1 | Crystal A | Printing section | 1.44 | 1.44 |
| Comparative Example 2-1 | Crystal B | Printing section | 1.44 | 1.44 |
| Comparative Example 2-2 | Crystal C | Printing section | 1.44 | 1.44 |
| Comparative Example 2-3 | None | Printing section | 1.44 | 1.40 |

The results shown in Table 3 above reveal the following. The absence of a storability improver leads to a reduction in the density of the printing section after storage, resulting in poor moisture-and-heat resistance. On the other hand, the presence of a storability improver allows the density of the printing section to be maintained even after storage (i.e., improves the moisture-and-heat resistance), and it can be seen that there is no difference in the effect of improving moisture-and-heat resistance among the various crystal forms of the storability improvers. This means that the printing-section storability provided by conventional crystal forms can be maintained, even in cases where the crystal form is changed from a conventionally-known form to the AO-30 crystal form according to the present invention.

TABLE 4

| | | | Heat resistance (density) | | | Moisture-and-heat resistance (density) | |
|---|---|---|---|---|---|---|---|
| | Storability improver | Area measured | Initial | Stored for 2 h at 80° C. | Stored for 2 h at 100° C. | Initial | Stored for 1 h at 60° C., 90% |
| Example 2-1 | Crystal A | Non-printing section | 0.04 | 0.12 | 1.12 | 0.04 | 0.07 |
| Comparative Example 2-1 | Crystal B | Non-printing section | 0.04 | 0.15 | 1.26 | 0.04 | 0.14 |
| Comparative Example 2-2 | Crystal C | Non-printing section | 0.04 | 0.14 | 1.17 | 0.04 | 0.09 |
| Comparative Example 2-3 | None | Non-printing section | 0.04 | 0.06 | 0.24 | 0.04 | 0.05 |

The results shown in Table 4 above reveal the following.

Evaluating the heat resistance of the non-printing section by comparing the density before storage ("Initial") and the density after storage for 2 hours at 100° C., Crystals B and C increase the density by 1.22 and 1.13, respectively, whereas Crystal A increases the density only by 1.08. This shows that Crystal A improves the heat resistance of the non-printing section and sufficiently improves the whiteness thereof, compared to Crystals B and C. Further, evaluating the moisture-and-heat resistance by comparing the density before and after storage, Crystals B and C increase the density by 0.10 and 0.05, respectively, whereas Crystal A increases the density only by 0.03. This shows that Crystal A improves the moisture-and-heat resistance by 40% compared to Crystal C which is one of the highly-effective comparative compounds, thus significantly improving the whiteness.

The above results significantly show that the AO-30 according to the present invention has usefulness as a storability improver, which conventional AO-30 crystals do not.

INDUSTRIAL APPLICABILITY

The present invention can provide a thermal recording material which includes, as a storability improver for the thermal recording material such as thermal recording paper, AO-30 having a specific crystal structure and trapping and containing water and/or methanol, and which thereby has improved heat resistance in non-printing sections while maintaining the moisture-and-heat resistance in printing sections, as compared to materials containing AO-30 of conventional crystal forms.

The invention claimed is:

1. A thermal recording material containing, as a storability improver, tris(2-methyl-4-hydroxy-5-t-butylphenyl)butane trapping and containing water and/or methanol and having a crystal structure that shows a maximum X-ray diffraction peak at a diffraction angle 2θ of 6.58° according to X-ray diffraction measurement using an X ray having a wavelength of a Cu—Kα line.

2. The thermal recording material according to claim 1, having a thermal-recording layer that contains the tris(2-methyl-4-hydroxy-5-t-butylphenyl)butane in an amount of 0.1 to 15% by mass with respect to the thermal-recording layer.

3. The thermal recording material according to claim 1, wherein the amount of the water and/or methanol trapped and contained in the tris(2-methyl-4-hydroxy-5-t-butylphenyl)butane is 0.1 to 10% by mass in total.

4. The thermal recording material according to claim 2, wherein the amount of the water and/or methanol trapped and contained in the tris(2-methyl-4-hydroxy-5-t-butylphenyl)butane is 0.1 to 10% by mass in total.

* * * * *